United States Patent
Pala

(10) Patent No.: US 12,268,371 B2
(45) Date of Patent: Apr. 8, 2025

(54) DEVICE AND METHOD FOR SALIVA-BASED ANALYTE TESTING

(71) Applicant: Clinical Reference Laboratory Inc., Lenexa, KS (US)

(72) Inventor: Serhat Pala, San Diego, CA (US)

(73) Assignee: Clinical Reference Laboratory, Inc., Lenexa, KS (US)

( * ) Notice: Subject to any disclaimer, the term of this patent is extended or adjusted under 35 U.S.C. 154(b) by 914 days.

(21) Appl. No.: 17/421,296

(22) PCT Filed: Jan. 10, 2020

(86) PCT No.: PCT/US2020/013222
§ 371 (c)(1),
(2) Date: Jul. 7, 2021

(87) PCT Pub. No.: WO2020/146826
PCT Pub. Date: Jul. 16, 2020

(65) Prior Publication Data
US 2022/0117588 A1    Apr. 21, 2022

Related U.S. Application Data

(60) Provisional application No. 62/879,437, filed on Jul. 27, 2019, provisional application No. 62/791,012, filed on Jan. 10, 2019.

(51) Int. Cl.
*A61B 10/00* (2006.01)
*B01L 3/00* (2006.01)
*G01N 1/18* (2006.01)

(52) U.S. Cl.
CPC ...... *A61B 10/0051* (2013.01); *A61B 10/0096* (2013.01); *B01L 3/5023* (2013.01);
(Continued)

(58) Field of Classification Search
CPC ............ A61B 10/0051; A61B 10/0096; A61B 2010/0003; A61B 2010/0009;
(Continued)

(56) References Cited

U.S. PATENT DOCUMENTS

2003/0027359 A1 * 2/2003 Hudak .................... B01L 3/502
436/518
2003/0064526 A1 4/2003 Niedbala et al.
(Continued)

FOREIGN PATENT DOCUMENTS

WO    WO2009073155    6/2009

*Primary Examiner* — Jill A Warden
*Assistant Examiner* — Jacqueline Brazin
(74) *Attorney, Agent, or Firm* — HOVEY WILLIAMS LLP

(57) ABSTRACT

A multi-chamber saliva-collection device is configured to segregate a saliva sample into at least two aliquots, each of the at least two aliquots being contained within a distinct chamber of the multi-chamber device, wherein the multi-chamber device is useful for performing an instant analyte test and a subsequent DNA confirmation to validate the identity of the tested individual. Related methods for using the device to obtain each of: an analyte test result, and a DNA confirmation of the identity of the individual from which the tested saliva sample, are also disclosed.

19 Claims, 12 Drawing Sheets

(52) U.S. Cl.
CPC ........ *G01N 1/18* (2013.01); *A61B 2010/0003* (2013.01); *B01L 2200/0689* (2013.01); *B01L 2300/044* (2013.01); *B01L 2300/0672* (2013.01); *B01L 2300/0825* (2013.01); *B01L 2300/0864* (2013.01); *B01L 2400/0683* (2013.01)

(58) Field of Classification Search
CPC .......... B01L 3/5023; B01L 2200/0689; B01L 2300/044; B01L 2300/0672; B01L 2300/0825; B01L 2300/0864; B01L 2400/0683; B01L 3/502; B01L 2400/065; G01N 1/18
USPC ........................................................ 600/573
See application file for complete search history.

(56) References Cited

U.S. PATENT DOCUMENTS

| | | | |
|---|---|---|---|
| 2007/0275475 A1* | 11/2007 | Liang | B01L 3/502 422/68.1 |
| 2008/0199851 A1* | 8/2008 | Egan | G01N 33/56983 435/5 |
| 2009/0013805 A1* | 1/2009 | Zollinger | G01N 1/2035 73/863.86 |
| 2009/0181451 A1* | 7/2009 | Slowey | B01L 3/5029 435/287.7 |
| 2015/0037830 A1* | 2/2015 | Jakobsen | G01N 1/28 435/307.1 |

* cited by examiner

DNA + DRUG Test Workflow

Step 0: Donor receives random automated request to take test or requested by Administrator (time limit)

Step 1: Donor opens the app and then opens SalivaConfirm Instant Device

Step 2: Donor enters the device unique label number or scans the barcode into the App Step 3: Donor start the test and give sample by following instruction

*Time stamp in App for Collection Time*

Step 4a: It can be only saliva collection and no instant result. If so record collection and verification of enough saliva sample recorded App Step 4b: It can be instant result with screening (if Instant result using Mobile App reads/takes picture of the result and uploads into system

*Mobile App or Admin Decides Action*

Step 5a: Donor sends the collection device with prepaid mailer

Step 5b: Donor discards the used test and test is completed

*Steps can be in either order*

Step 6: Sample received at the laboratory (DNA) and DNA Profile match is done

Step 7: Drug test laboratory result is processed to determine positive or negative Step 8: Laboratory result - MRO Review and Result Publish in Online Account

FIG.12

DEVICE AND METHOD FOR SALIVA-BASED ANALYTE TESTING

TECHNICAL FIELD

The invention relates to devices and methods for analyte testing, such as, for example and not limitation, drug testing; and more particularly, to a multi-chamber device configured to segregate a saliva sample into at least two aliquots for use in performing an instant analyte test and a subsequent DNA confirmation to validate the identity of the tested individual, and related methods.

BACKGROUND ART

Instant saliva tests are currently used in multiple settings for a variety of purposes, such as: (i) employers testing prospective or existing employees at a workplace to make sure they are not abusing a particular substance; (ii) family members and friends testing other family members or friends to make sure they are not abusing a particular substance; (iii) law enforcement officials testing individuals to verify the individual in question is not abusing a particular substance; (iv) healthcare providers testing an individual to insure that the individual is not abusing a particular substance; and/or (v) healthcare providers testing an individual to make sure the individual is taking a prescribed medication.

There are three conventional methods employed for testing purposes, including:

Instant Result Test (IRT):

In this method, a saliva sample is collected, and the collected saliva sample is tested using instant test strips. The test strips will show a positive, negative or invalid result upon contacting the saliva sample.

This method is used mainly because it is the least costly, and because it is the easiest way one can ensure the identity of the saliva-donor of the sample since a collector of the sample can observe the saliva-donor while the sample is collected. Here, there is no chain of custody required for the sample, since the sample is not subsequently confirmed with laboratory-based testing.

One disadvantage of this method is that test strips, even those of the highest quality, have a chance of providing a false positive, false negative or invalid result. The invalid result can be due to an insufficient saliva sample, corrupted chemicals or the condition of the saliva. Accordingly, this method is not as reliable and accurate as laboratory testing of a saliva sample.

Another important disadvantage of this testing method is that if an action is required due to the result of the test (such as, for example, termination of employment), it would be difficult to justify that action because the tested individual can allege that the sample was not their own, or that the result was due to false positive. This method does not allow for proof that the saliva came from the individual, i.e. the saliva-donor. Unless the saliva is preserved in a particular way, it would be difficult to use the same saliva to run a DNA profile test for validating identity of the saliva source.

Instant Result Test Followed by a Laboratory Confirmation (IRT+LC):

The instant test process described above is often used as a screening tool. In most cases, only when the instant test strip indicates a non-desired result (usually a positive result), is the sample sent to a laboratory for confirmation with sophisticated lab equipment that can give a definitive result.

The main advantage of this process is that it can ensure 100% accuracy without the risk of a false positive or false negative. In most cases there is also a quantified result that indicates the level of the substance being tested for.

However, the collector and the administrative entity must accurately track and ensure chain of custody of the sample, at all times during the sample collection and testing process. Once the saliva sample is collected, there must be a trusted collector tasked with verifying the identity of the saliva-donor, and then guarantee the sample is not tampered with throughout the transportation of the sample to the laboratory and throughout the sample testing process within the laboratory. Even if the chain of custody is followed, there may still be still inaccuracies and mistakes in the process due to things like, for example, use of false identification by the saliva-donor, human errors throughout the collection, shipping, receiving and processing of the sample, or fraud.

Laboratory Testing of Saliva Sample (LT):

Another common method used for saliva sample testing includes collection of a saliva sample from an individual using a saliva collection device, and laboratory testing without any instant test being conducted. All of the above advantages and disadvantages of Instant Result Test Followed by a Laboratory Confirmation ("IRT+LC") also exist with this method.

An advantage over IRT+LC, as described above, is that there will not be a screening process that can lead to false positives or negatives in the instant results that could cause some samples not to be sent to a laboratory for confirmation, since all samples that are collected will be subsequently tested.

A disadvantage of this method over the IRT+LC is an additional cost and added resources of collection, shipping and processing of laboratory testing for each sample rather than a smaller screened number of samples.

A key limitation of performing saliva-based testing of a substance ("analyte") at a laboratory (such as drug metabolites), is that most analyte testing done at laboratories requires a different sample collection and preservation method with a chemical buffer agent for the analyte testing than the sample collection and preservation method with a chemical buffer agent required DNA profile testing. This makes it difficult to use the same saliva sample for analyte testing and collateral DNA profile testing in the laboratory.

SUMMARY OF INVENTION

Technical Problem

In addition to the problems and limitations described in the Background Art, above, there is currently no saliva sample collection device and corresponding method for efficiently obtaining a saliva sample from an individual, providing an instant result, and biologically-protecting, and also preventing tampering of the sample while contained in the collection device, such that the device may be delivered to a laboratory for subsequent analyte and DNA-based confirmations.

Solution to Problem

Herein disclosed is a multi-chamber device configured to segregate a saliva sample into at least two aliquots, each of the at least two aliquots being contained within a distinct chamber of the multi-chamber device, for use in performing an instant analyte test and a subsequent DNA confirmation to validate the identity of the tested individual.

Also disclosed are methods for using the device to obtain each of an analyte test result and a DNA confirmation of the identity of the individual from which the tested saliva sample originated.

Advantageous Effects of Invention

Practicing the embodiments of the invention, each of a saliva-based analyte test, such as a test for the presence of an illicit drug substance in the saliva of a saliva-donor, and a DNA confirmation test for confirming an identity of the saliva-donor, are completed without costly expenditure of resources, including monetary and time resources.

Chain of custody of the sample is achieved via saliva collection device protections, such as saliva segregation and tamper proofing elements. This eliminates many of the chain of custody-related issues with respect to conventional collection devices.

The saliva-donor may perform the test independently from a collector, since, the test is based on DNA confirmation of the saliva-donor. Accordingly, the saliva sample can be collected remotely, without supervision and identity verification offered by a collector. In addition, time and monetary resources attributed to collector test-administration and supervision can be eliminated from the process.

BRIEF DESCRIPTION OF DRAWINGS

The detailed description is described with reference to the accompanying figures of the drawings. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed methods may be performed in an arbitrary order, unless otherwise provided in the claims.

FIG. 12 shows a schematic of an example testing workflow using the device and methods disclosed herein.

DESCRIPTION OF EMBODIMENTS

Figure 1:
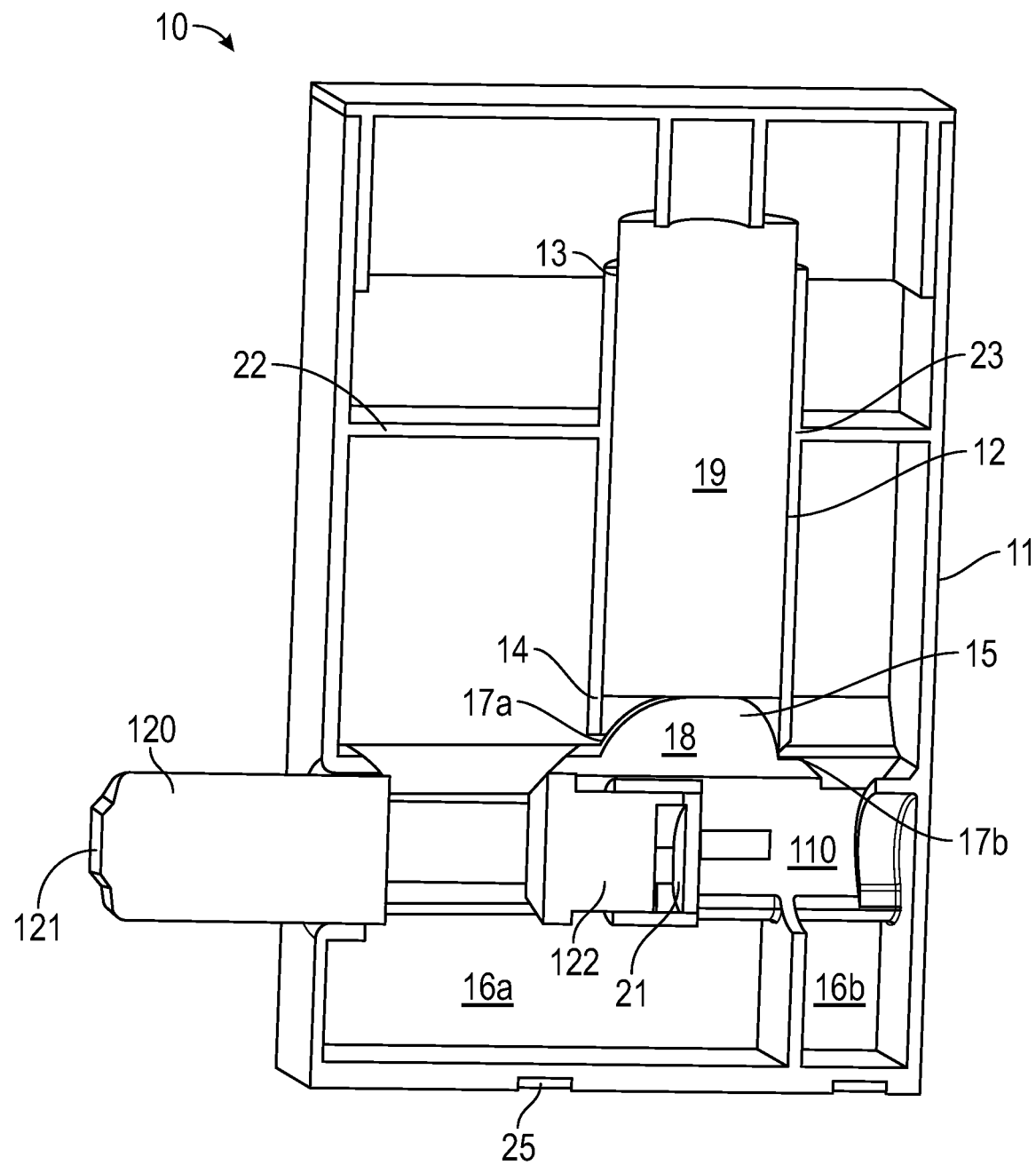
FIG. 1 shows a multi-chamber device in accordance with a first illustrated embodiment, the device being configured for saliva sample collection, and saliva-based analyte testing, with a segregated sample stored with a DNA preservation buffer in a second chamber for subsequent verification of donor-identity.

In the following description, for purposes of explanation and not limitation, details and descriptions are set forth in order to provide a thorough understanding of the embodiments of the invention. However, it will be apparent to those skilled in the art that the present invention may be practiced in other embodiments, including certain variations or alternative combinations that depart from these details and descriptions. The examples disclosed herein are intended to enable those with skill in the art to practice the invention, but such examples shall not reasonably be construed as limiting the spirit and scope of the invention as-claimed.

General Disclosure

The invention may be practiced in a number of embodiments that can be configured to provide a multi-chamber device, including two or more (three, four, five, . . . N) chambers within the container, wherein the two or more chambers are each configured to capture an aliquot of a saliva sample obtained from a saliva-donor. Each of the chambers may be configured to receive, in addition to the aliquot of saliva, a preservation buffer, such as a DNA preservation buffer for inhibiting enzymatic degradation of the saliva sample, or other preservation-related buffer, which can be combined with the saliva aliquot. In this regard, an instant test result may be provided, for example, via lateral flow immunochromatographic diagnostic assay or other field-based assay, and an amount of the saliva sample may be preserved for subsequent confirmation of test results and verification of donor identity, for example, via DNA analysis.

Thus, in each of the illustrated embodiments, with reference to FIGS. 1-10, and other embodiments which are not illustrated herein, a multi-chamber saliva collection device (10) is disclosed, comprising: a container (11) including: a well (12) extending within a volume of the container from a proximal end (13) to a distal end (14), a bifurcating element (15) disposed adjacent to the well at the distal end, a first chamber (16a) coupled to the bifurcating element at a first fluid-aperture (17a), and a second chamber (16b) coupled to the bifurcating element at a second fluid-aperture (17b), a volume between each of: the well, the first fluid-aperture and the second fluid-aperture collectively defining a fluid communication channel (18); wherein the container is adapted to receive saliva (SA) upon extraction from a collection-swab (19), and communicate said saliva through the fluid communication channel into each of the first and second chambers; characterized in that the device further comprises: an amount of DNA preservation buffer (20) contained within a buffer-containing cavity (21); the buffer-containing cavity being configured to selectively release the DNA preservation buffer for mixing with an aliquot of the saliva in at least one of the first and second chambers.

The device may further comprise a top-plate (22), the top-plate embodying a swab-aperture (23), wherein the swab-aperture is configured to pass at least a portion of a collection-swab through a surface of the top-plate.

The proximal end of the well can be coupled to the top plate at the swab-aperture.

The device may further comprise a lateral flow immunochromatographic diagnostic assembly (24) coupled to the first chamber in fluid communication therewith, wherein the lateral flow immunochromatographic diagnostic assembly is configured to receive an effective amount of saliva from the first chamber for completing a lateral flow immunochromatographic diagnostic test and displaying results thereof.

The device may further comprise an access-port (25) embodied within the container at one of the first and second chambers, wherein the access-port is configured for accessing, from outside the container, the respective aliquot of the saliva contained in the one of the first and second chambers.

In the various embodiments for practicing the invention, any DNA preservation buffer may be utilized in accordance with the knowledge, resources and ability of a skilled artisan. Likewise, any field test for testing analyte within the saliva sample may be implemented as would be appreciated by one with skill in the art. Thus, detailed specifications of the DNA preservation buffer and the instant result test are being omitted as a myriad of variations may be similarly implemented and each is derived from a general knowledge and skill in the art.

Each of the embodiments disclosed herein references a number of features of one or more embodiments. It should be understood that the invention may be practiced in any embodiment, whether explicitly described herein or not, that substantially achieves the function of providing an instant results test and/or a laboratory confirmation of the results, in combination with a DNA confirmation indicating a source of the saliva-sample (saliva-donor identity), and includes any combination or arrangement of at least a portion of the features disclosed herein.

Now we turn to the drawings, with particular reference to illustrated embodiments, we turn to the drawing.

Example 1: Device w/Trigger Lock Assembly

Figure 2:
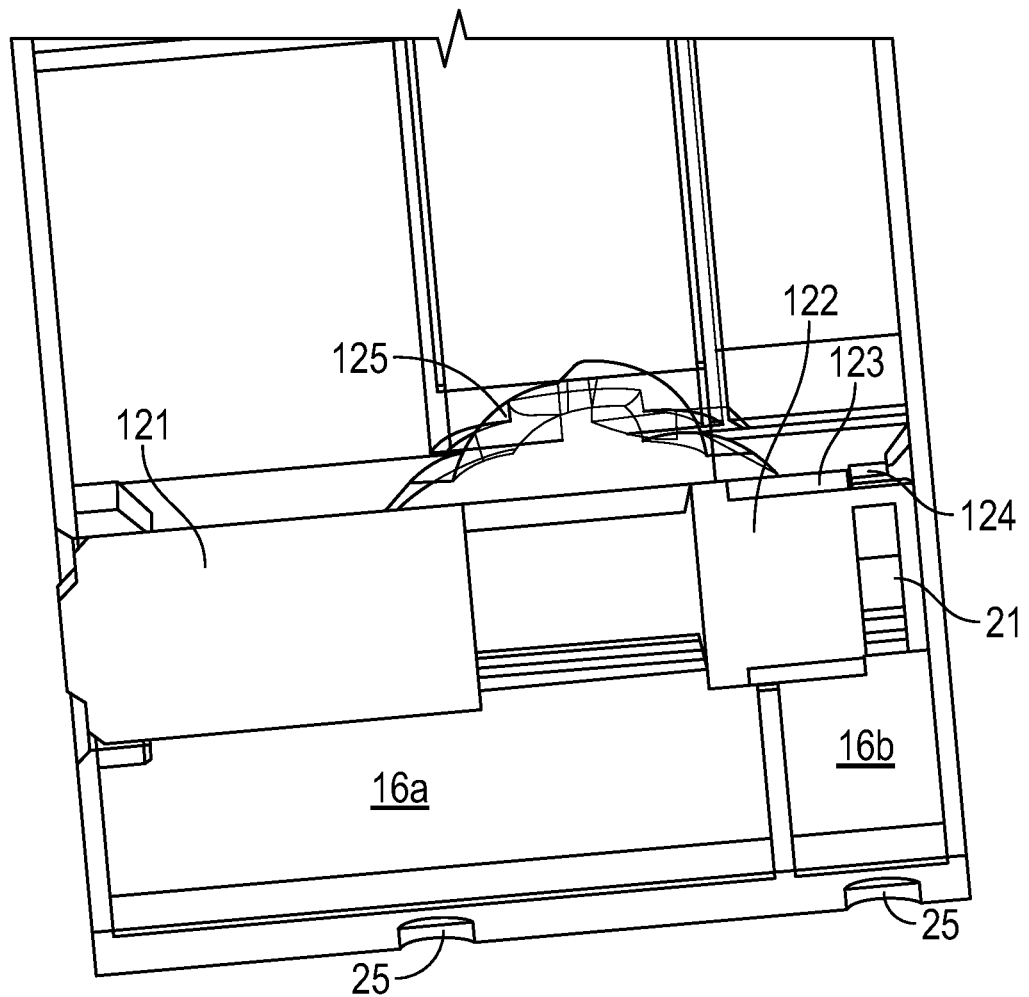
FIG. 2 shows a zoomed view of a trigger for releasing the DNA preservation buffer into a second chamber where it may combine with a saliva sample aliquot and be stored for subsequent use.

A first illustrated embodiment is illustrated in FIGS. 1-2.

FIG. 1 shows a multi-chamber device in accordance with a first illustrated embodiment, the device being configured for saliva sample collection, and saliva-based analyte testing, with a segregated sample stored with a DNA preservation buffer in a second chamber for subsequent verification of donor-identity.

FIG. 2 shows a zoomed view of a trigger for releasing the DNA preservation buffer into a second chamber where it may combine with a saliva sample aliquot and be stored for subsequent use.

While the DNA preservation buffer is not shown, the DNA preservation buffer will be understood as being stored within the buffer-containing cavity (21) until released. Release of the DNA preservation buffer, in this first illustrated embodiment, is achieved with the trigger (120) pressed into the device such that the sleeve-seal (123) is released by the protrusion (124).

In accordance with the first illustrated embodiment, with reference to FIGS. 1-2, a multi-chamber saliva collection device (10), is disclosed in accordance with the features in the above General Disclosure, which is incorporated here by reference.

In the first illustrated embodiment, the device further comprises a horizontal channel (110), the horizontal channel coupled to the distal end of the well at a first side of the horizontal channel, and further coupled to the second chamber at a second side of the horizontal channel, wherein the first side of the horizontal channel is opposite the second side; and wherein a volume between each of: the well, the horizontal channel, the first fluid-aperture and the second fluid-aperture collectively defines the fluid communication channel.

Additionally, the device in the first illustrated embodiment further comprises a trigger-element (120) including: a protruding end (121) and a terminal end (122), wherein the protruding end is configured to extend through the container and is configured to be pressed toward the container for translating the trigger-element longitudinally along the horizontal channel, and wherein the terminal end of the trigger-element is configured to be contained within the container and further comprises: the buffer-containing cavity, and the DNA preservation buffer within the buffer-containing cavity.

The device in the first illustrated embodiment further comprises a sleeve-seal (123), the sleeve-seal being concentrically nested about the terminal end of the trigger and configured to establish a seal for containing the DNA preservation buffer within the buffer-containing cavity.

The device in the first illustrated embodiment further comprises a protrusion (124) extending from the container within the fluid communication channel and being disposed adjacent to a terminal end of the horizontal channel, wherein upon translation of the trigger the protrusion is configured to engage the sleeve-seal for releasing the DNA preservation buffer from within the buffer-containing cavity.

The bifurcating element can be configured as a dome having a gradual surface (125) for biasing flow of saliva in greater quantity toward the first chamber.

The device is configured such that, wherein upon releasing the DNA preservation buffer from within the buffer-containing cavity, the container is adapted to communicate the DNA preservation buffer through the fluid communication channel and into the second chamber for mixing with the aliquot of saliva therein.

Example 2: Device with Buffer-Containing Cap

A second illustrated embodiment is illustrated in FIGS. 3-10.

Figure 3:
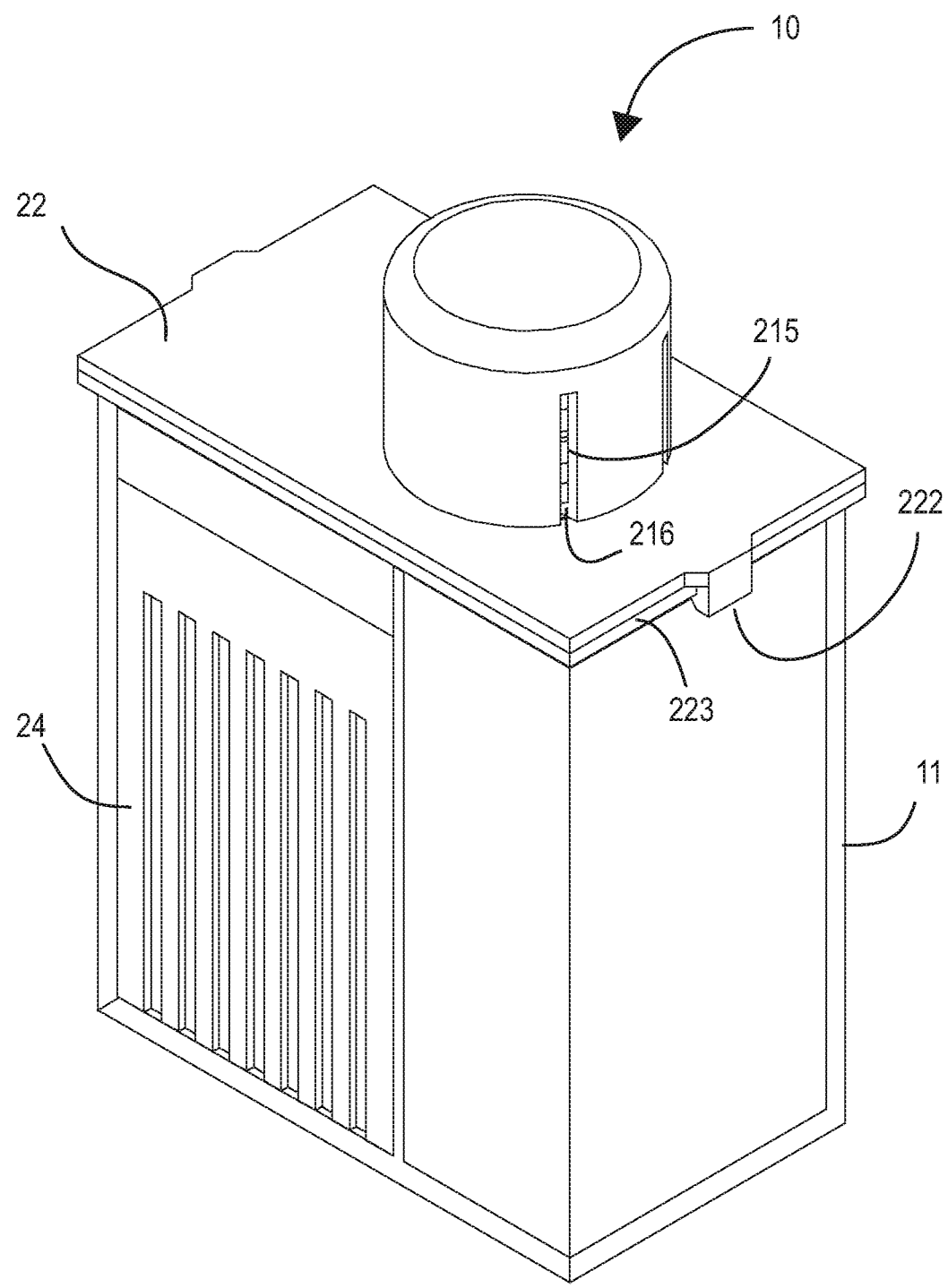
FIG. 3 shows a multi-chamber device in accordance with a second illustrated embodiment, the device being configured for saliva sample collection, and saliva-based analyte testing, with a segregated sample stored with a DNA preservation buffer in a second chamber for subsequent verification of donor-identity.

FIG. 3 shows a multi-chamber device in accordance with a second illustrated embodiment, the device being configured for saliva sample collection, and saliva-based analyte testing, with a segregated sample stored with a DNA preservation buffer in a second chamber for subsequent verification of donor-identity. Notable with reference to FIG. 3 is the slot (215) and tab (216), which can be positioned on either of the cap-element and the threaded-base. Here, the cap-element includes the tab (216), which is clearly viewed. However, the slot (215), is obstructed. The slot is essentially a vertical portion of the threaded-base where threads are removed, such that the tab (and cap-element) can continue downwardly along the threaded-base. In this regard, the cap-element can be rotated to align the tab with the slot before the cap-element may continue downwardly and puncture the film-element for releasing the DNA preservation buffer.

Figure 4:
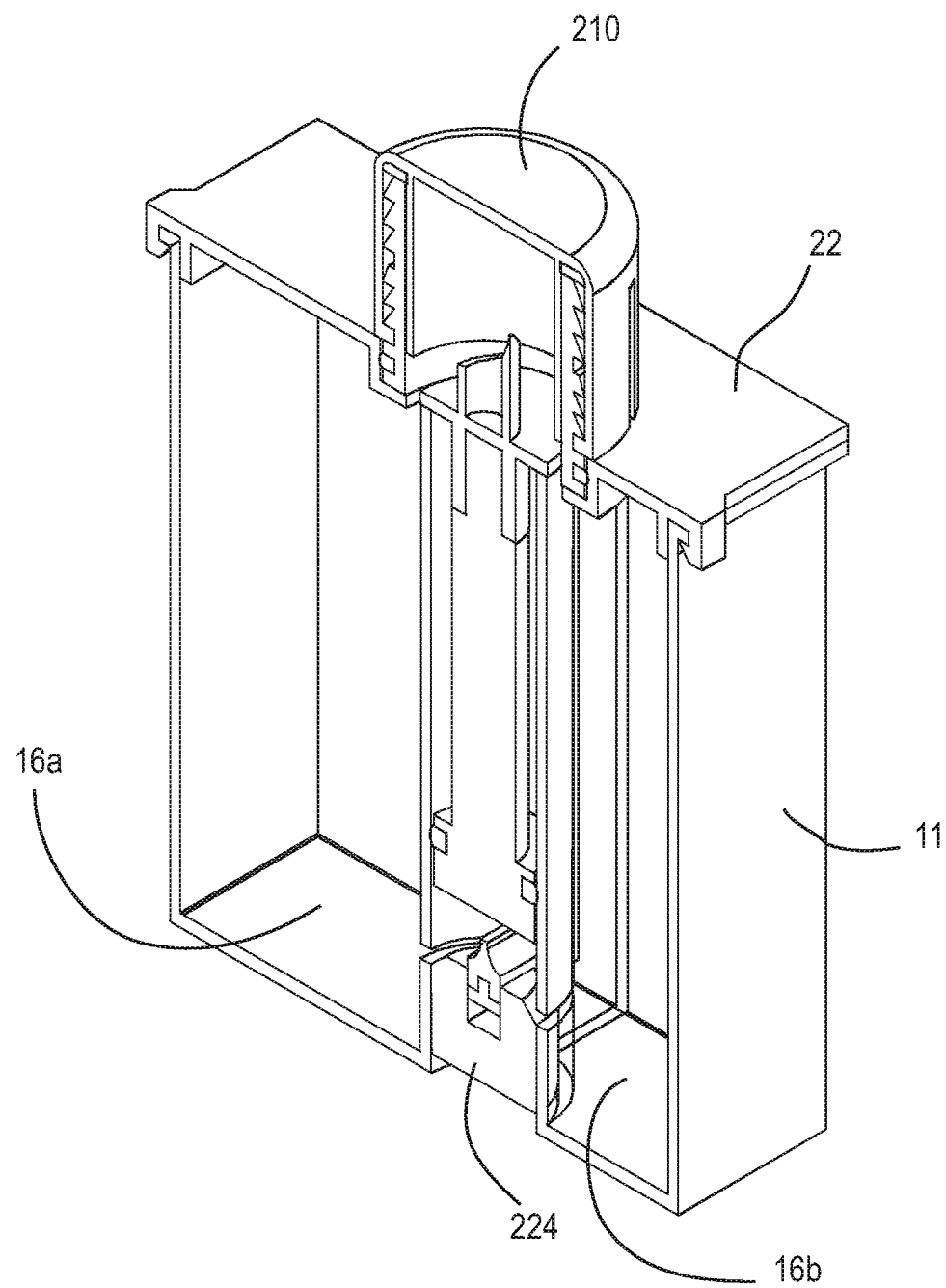
FIG. 4 shows a perspective view of a sectioned device in accordance with the second illustrated embodiment.

FIG. 4 shows a perspective view of a sectioned device in accordance with the second illustrated embodiment.

Figure 5:
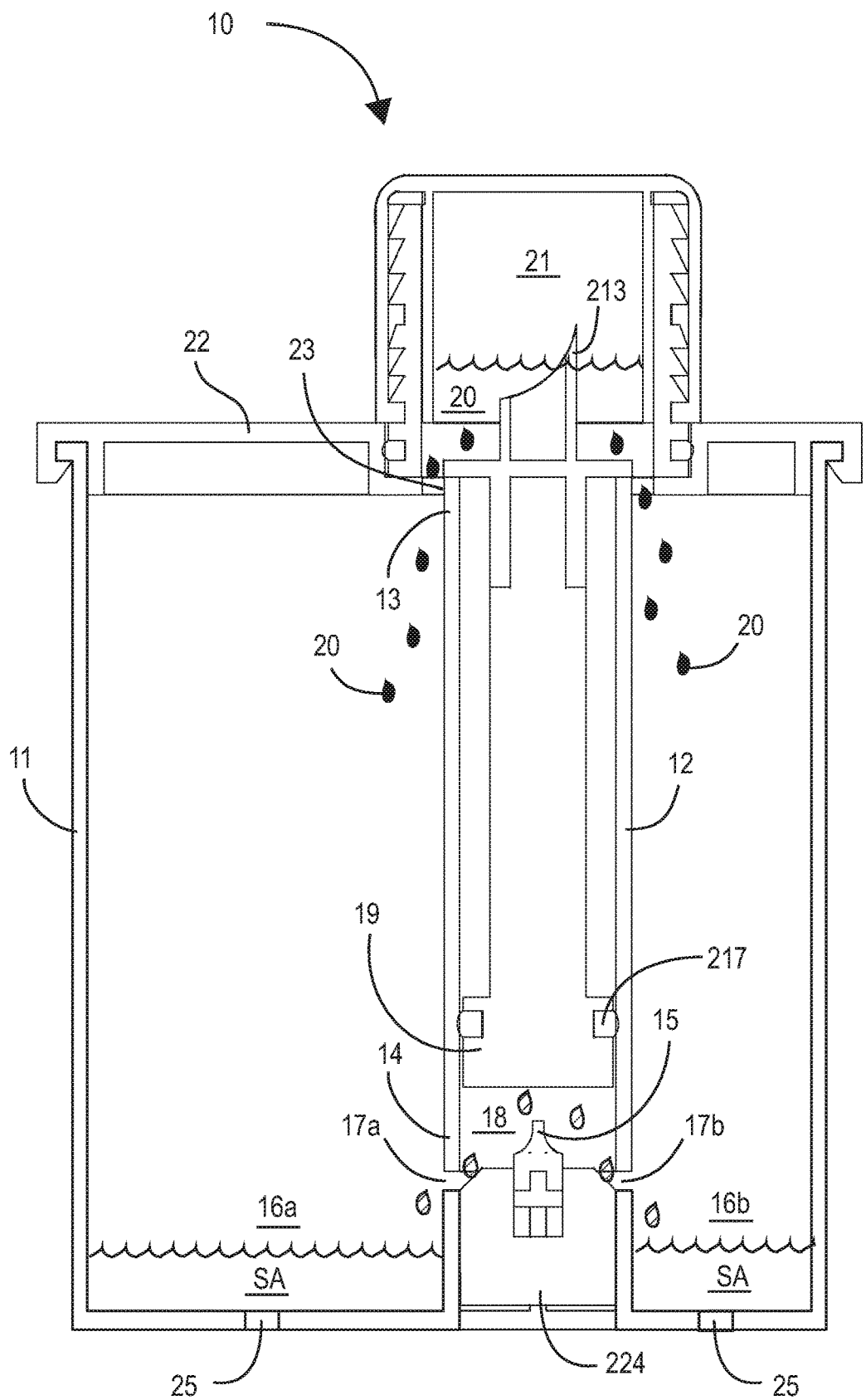
FIG. 5 shows a front view of a sectioned device in accordance with the second illustrated embodiment.

FIG. 5 shows a front view of a sectioned device in accordance with the second illustrated embodiment. With the cap-element positioned such that the puncture element breaks the film-element, the DNA preservation buffer is released and flows with gravitational force into one or more of the first and second chambers, depending on structural elements and configurations of the various apertures and channels within the device. Solid black droplets are illustrated to represent the DNA preservation buffer, and droplets with horizontal slashes are illustrated to represent flow of the saliva sample.

Figure 6:
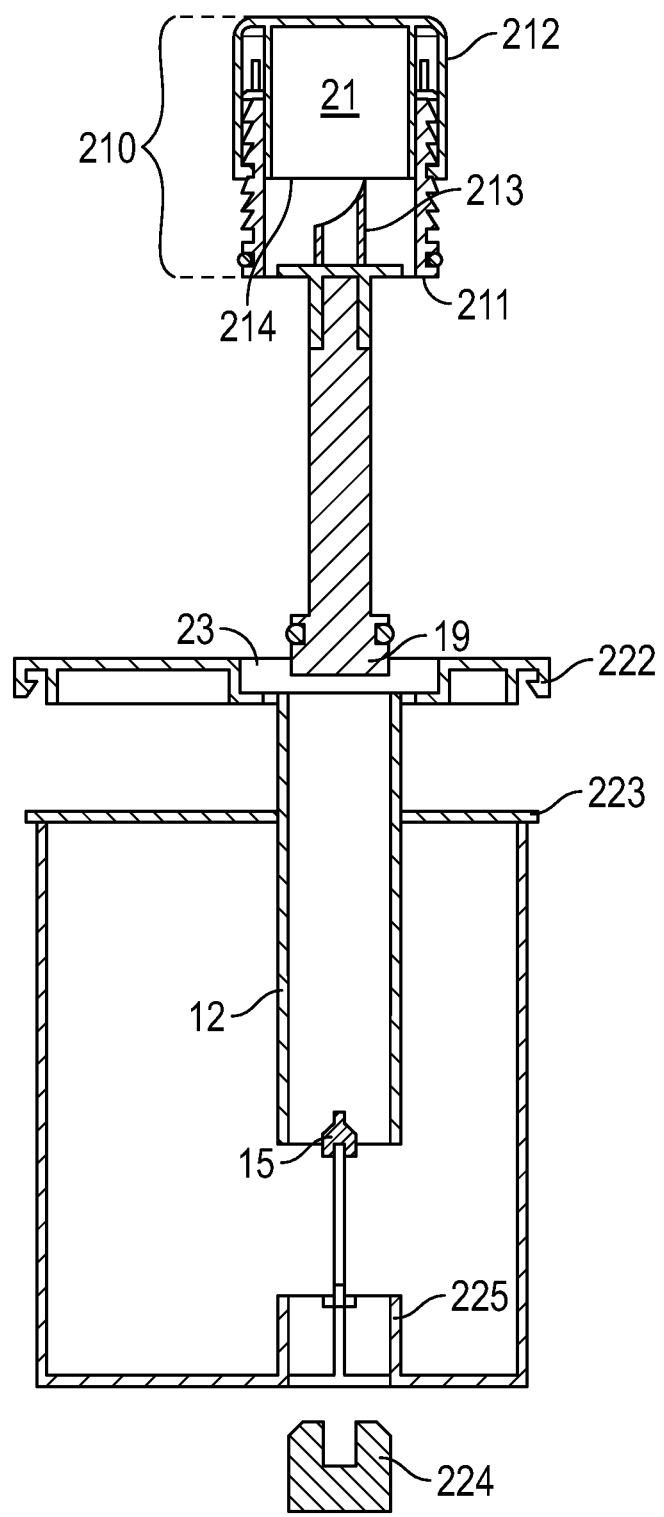
FIG. 6 shows an exploded view of a sectioned device in accordance with the second illustrated embodiment.

FIG. 6 shows an exploded view of a sectioned device in accordance with the second illustrated embodiment. Here, the buffer-containing cavity is intact (film element is not yet punctured) and contains the DNA preservation buffer.

Figure 7:
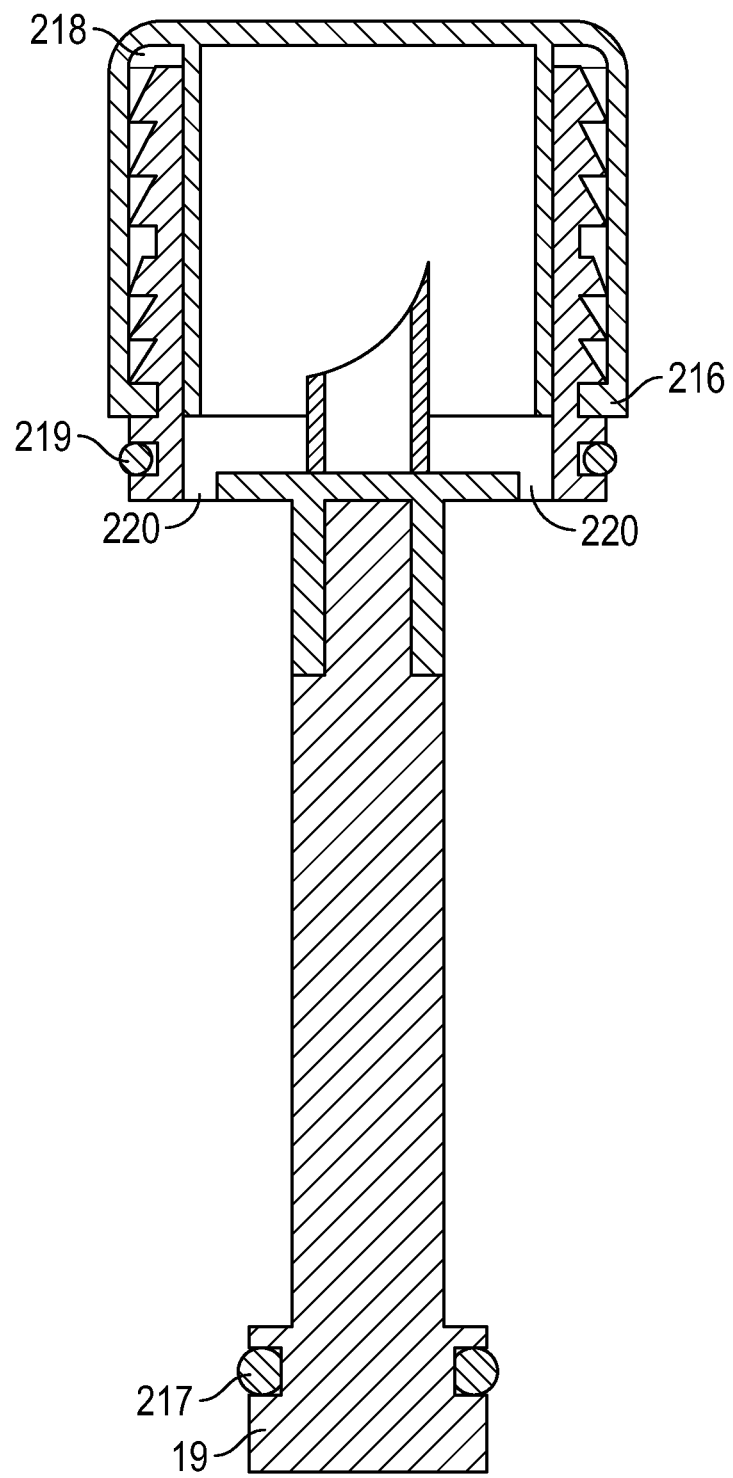
FIG. 7 shows a cap assembly and collection-swab in accordance with the second illustrated embodiment.

FIG. 7 shows a cap assembly and collection-swab in accordance with the second illustrated embodiment.

Figure 8:
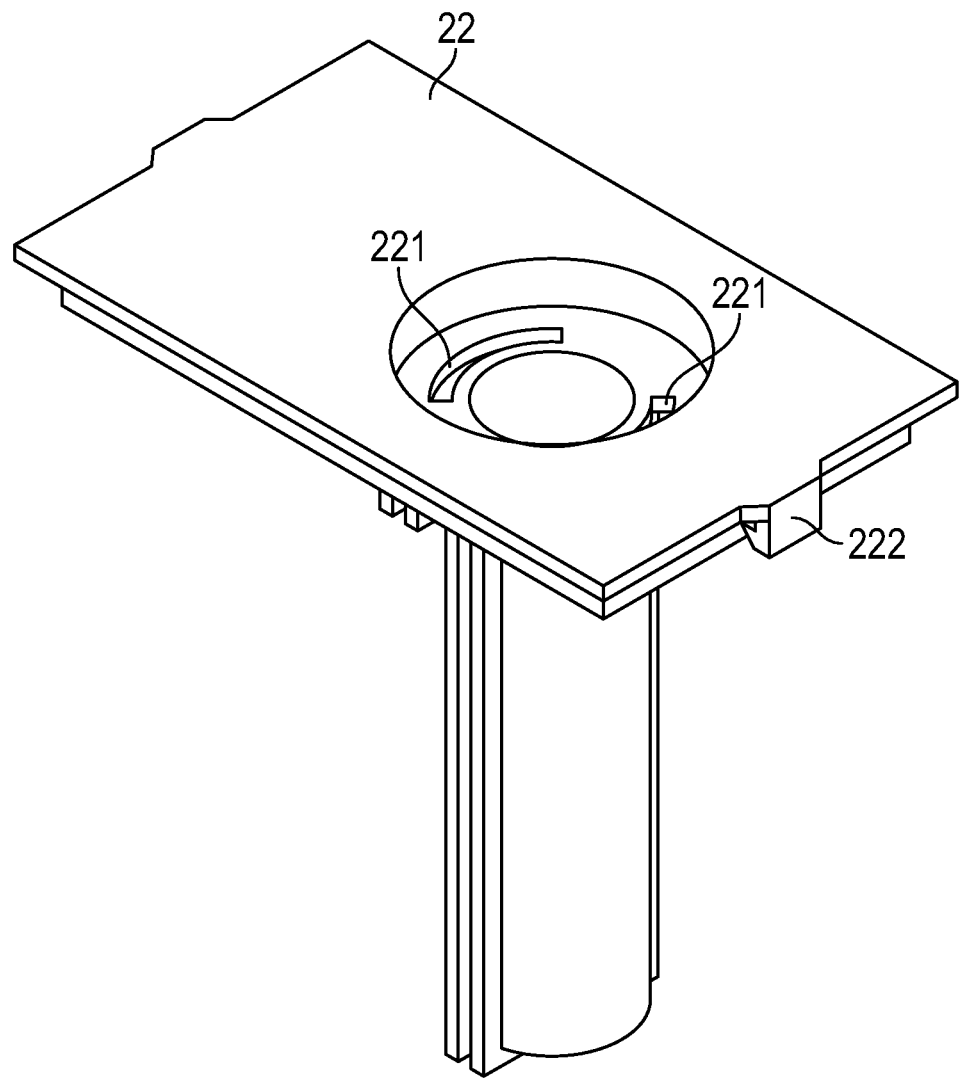
FIG. 8 shows a top-plate, swab-aperture, well, and other features of the device in isolation and in accordance with the second illustrated embodiment.

FIG. 8 shows a top-plate, swab-aperture, well, and other features of the device in isolation and in accordance with the second illustrated embodiment. Plates may extend from an outer-surface of the well, such as from the illustrated grooves of the well, to the various walls of the container forming each of the first and second chambers as a distinct liquid-tight volume.

Figure 9:
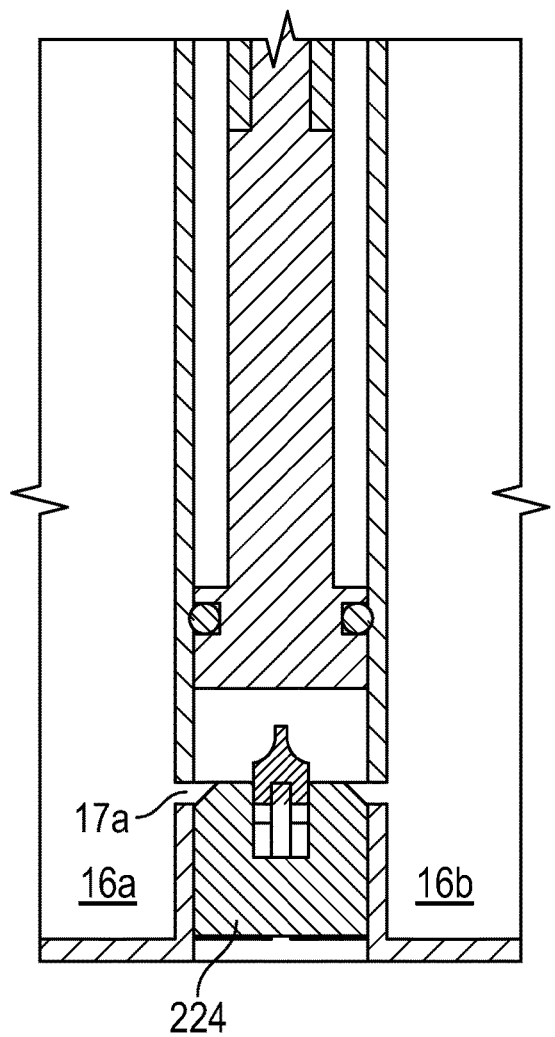
FIG. 9 shows a chamber seal of the device in an open configuration and in accordance with the second illustrated embodiment.

FIG. 9 shows a chamber seal of the device in an open configuration and in accordance with the second illustrated embodiment.

Figure 10:
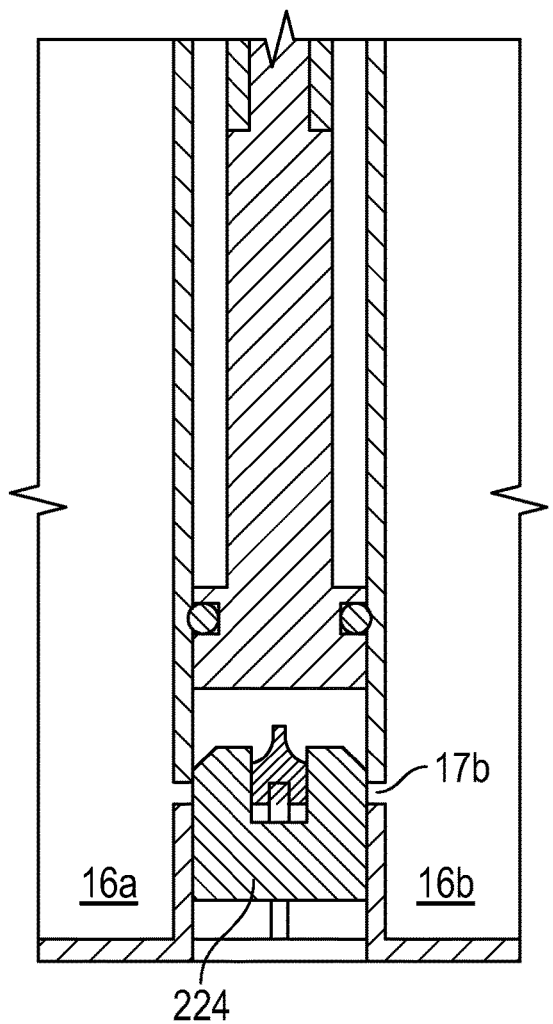
FIG. 10 shows a chamber seal of the device in a closed configuration and in accordance with the second illustrated embodiment.
Figure 11:
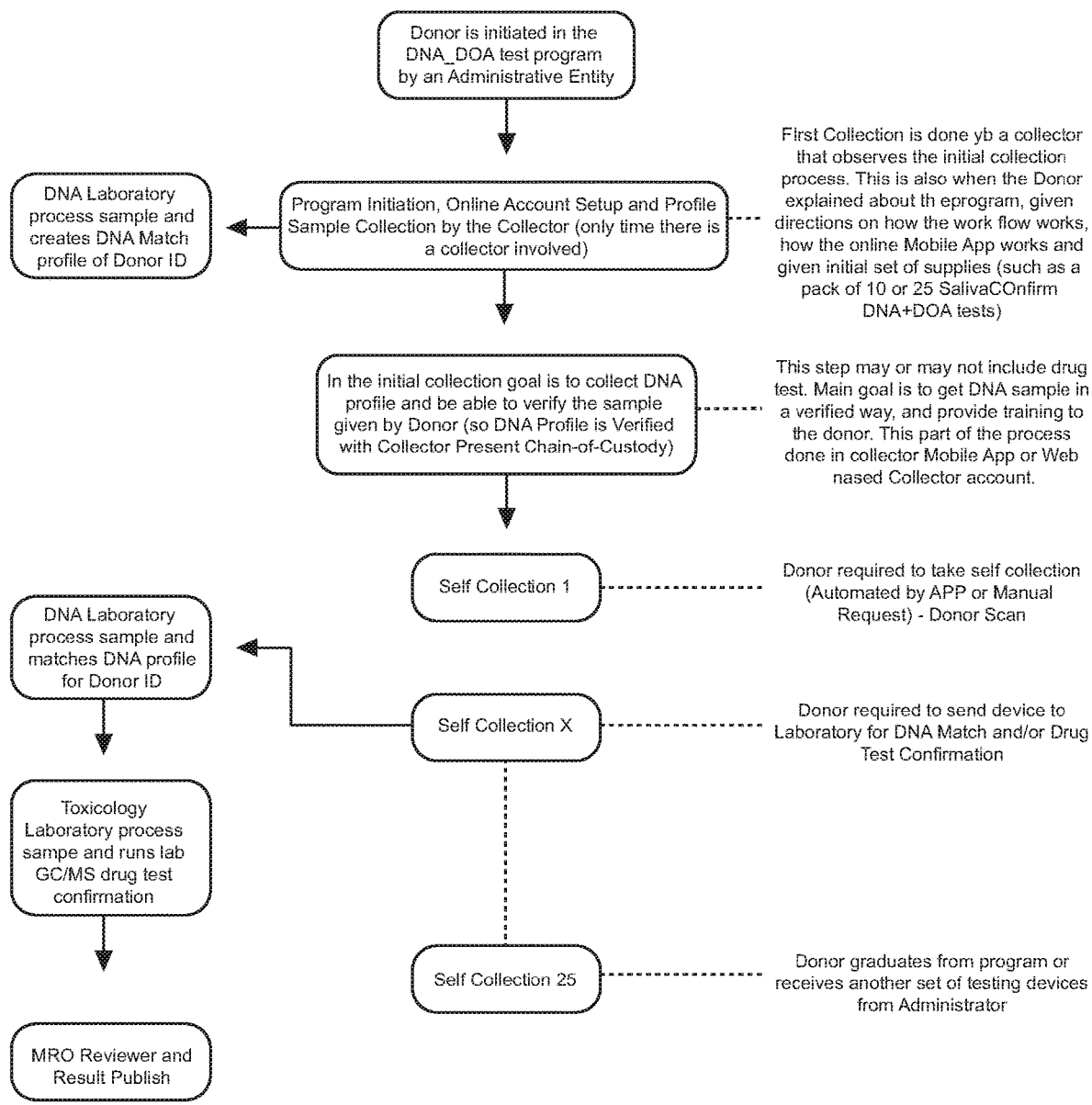
FIG. 11 shows a schematic of an example testing combination using the device and methods disclosed herein.
Figure 13:
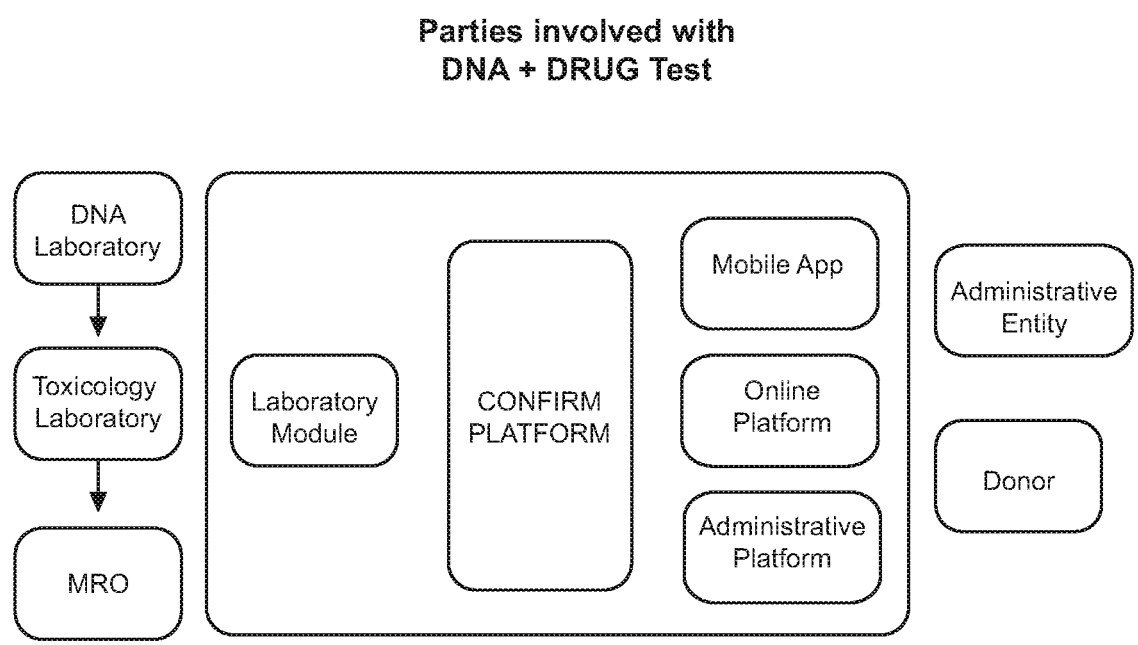
FIG. 13 shows a schematic representing various parties involved with DNA and analyte testing.

FIG. 10 shows a chamber-seal of the device in a closed configuration and in accordance with the second illustrated embodiment. Here, the chamber-seal is simply pressed into the device container to close the chamber-seal.

In accordance with a second illustrated embodiment, with reference to FIGS. 3-10, a multi-chamber saliva collection device (10), is disclosed in accordance with the features in the above General Disclosure, which is incorporated here by reference.

In the second illustrated embodiment, the device further comprises a cap-assembly (210), the cap-assembly including: a threaded-base (211) and a cap-element (212) coupled thereto; the threaded-base further comprising a puncture element (213); and the cap-element further comprising a film-element (214) sealed along a periphery of the cap-element; wherein a volume between an inside of the cap-element and the film-element defines the buffer-containing cavity, and the DNA preservation buffer is disposed within the buffer-containing cavity; and wherein, upon pressing the cap element against the threaded-base, the puncture element is adapted to puncture the film-element for releasing the DNA preservation buffer from the buffer-containing cavity.

In the second illustrated embodiment, the one of the threaded-base and the cap-element further comprises at least one slot (215), and the other of the threaded-base and cap-element further comprises at least one tab (216), wherein the cap-element is adapted to collapse against the threaded-base only when the at least one tab is rotationally aligned with the at least one slot, and wherein the film-element is adapted to be punctured by the puncture element only when the cap-element is collapsed against the threaded base.

The device in the second illustrated embodiment further comprises a first O-ring (217) configured to be disposed at a distal end of the collection-swab for establishing a first fluid-seal with an inner-surface of the well, a second O-ring (218) configured to be disposed between the threaded-base and the cap-element for establishing a second fluid-seal therebetween, a third O-ring (219) configured to be disposed between the threaded-base and the top-plate for establishing a third fluid-seal therebetween, or a combination thereof.

The threaded-base further comprises one or more buffer-ports (220), and said top-plate further comprising one or more buffer-channels (221) wherein the device is configured to direct a flow of the DNA preservation buffer from the buffer-containing cavity, through the buffer ports and the buffer channels, and into at least one of the first and second chambers.

The top-plate comprises one or more clips (222) for securing the top-plate to a rim (223) of the container.

The device according to according to the second illustrated embodiment further comprises a chamber-seal (224), the chamber-seal configured to be pushed into the container from a bottom end thereof, wherein, when pushed into receiver (225) of the container, the chamber seal is configured to form a seal at each of the first fluid-aperture and the second fluid-aperture, thereby segregating aliquots within each of the first and second chambers.

Example 3: Methods

The multi-chamber device can test for the presence of substances while also being configured to verify the identity of the donor of the sample by following the process laid out below:

Process Elements (1) DNA Profile (DP):

The donor will need to have a DP on record that the testing administrator has access to. The DP can either by created with data from a verified source or one can be created with a verified sample collection that has been authenticated by a verified sample collector and an official piece of identification.

(2) Sample Collection Device:

The donor will require a saliva collection device that splits the collected saliva into two chambers:

Chamber 1: An instant test may or may not be conducted with this sample for the presence of any particular substance with a given cut-off level.

Chamber 2: A saliva collection chamber that is used to later test the DNA profile to authenticate that the sample in Chamber 1 belongs to the donor.

An optional chemical buffer liquid will be released from componentry of the device as a part of the testing process. The device has two versions:

Version 1: comes with instant test strips that can be used as a screening tool.

Version 2: designed to be used as a collection kit for the saliva sample to be tested at the laboratory for both substances and for DNA matching purposes.

A Unique Identifier Label Number (UILN):

Each test will have a UILN visually present on the front of the device. This number will be used as a specimen ID number and with the use of and accompanying mobile app may also verify the sample collection time.

Collection Assistant Mobile App (the App):

This collection assistant mobile app might be used to record the sample collection by the individual, assist the donor with the collection process, record the time and date of the sample collection, and assist with all other collection workflow related aspects.

Results Database (RD):

There will be a database maintained to upload the results for the donors and administrative entities. This database will be available online through a secure website.

Example 4: Self Testing w/Instant Result

Step 1: DNA Profile Collection or DNA Profile Database Access:

The Administrative Entity acquires a DNA profile for the Donor either by accessing a database that has the verified DNA profile of the donor on record or by creating a DNA profile of the person with a verified sample collection to be tested for DNA specifically. Once a DNA profile is procured, it is added to our secure DNA profile database for future reference.

Step 2: Saliva Collection with Instant Result:

The donor opens the app and then opens the device package. From the donor's account on the app, donor either enters the UILN or scans the package's barcode. The donor can then start the testing process. The donor follows the instructions in the package to collect the saliva sample and completes the test. The donor then takes a picture of the instant test strip result and uploads the photo with result into the app. Time of the testing is recorded (to note the exact moment of saliva collection) and ensure that the donor does not conduct the test multiple times and chooses the sample they want to use for the record.

Step 3: Laboratory Confirmation:

If necessary, the sample is sent to the laboratory to process and test it for the presence of the substance being tested for. This will depend on the result from Step 2, and how the administrative entity prefers the testing process to be done. The administrative entity may want to further test samples that provide only positive results or negative results.

Depending on the preference of the administrative entity, either all samples collected get processed for DNA testing, or only ones that have a specific result (positive or negative) or a number of random samples. The DNA testing can be done at the same laboratory or a partner laboratory at a different location.

Step 4: Test Result Delivery:

Depending on the preference of the administrative entity, results will be posted to the secure results database with or without DNA profile matching.

Example 5: Self Testing with DNA Collection

Step 1: DNA Profile Collection or DNA Profile Database Access:

The administrative entity acquires a DNA profile for the donor either by accessing a database that has the verified DNA profile of the donor on record or by creating a DNA profile of the person with a verified sample collection to be tested for DNA specifically. Once a DNA profile is procured, it is added to the secure DNA profile database for future reference.

Step 2: Saliva Collection Only:

The Donor either registers the UILN on the app or with another form of online access to the results database. This will ensure results from the testing process will be attributable to the donor. The donor follows the instructions in the package to collect the saliva sample. The donor completes the test and sends the sample to the laboratory.

Step 3: Laboratory Confirmation:

The laboratory processes the saliva sample for the presence of the drug or substance being tested for.

Depending on the preference of the administrative entity, either all samples collected get processed for DNA testing, or only ones that have a specific result (positive or negative) or a number of random samples. The DNA testing can be done at the same laboratory or a partner laboratory.

Step 4: Test Result Delivery:

Depending on the preference of the administering entity results will be posted to the secure results database with or without DNA profile matching.

Example 6: Collector Testing with Instant Result or DNA Collection

Step 1: DNA Profile Collection or DNA Profile Database Access:

The administrative entity acquires a DNA profile for the Donor either by accessing a database that has the verified DNA profile of the donor on record or by creating a DNA profile of the person with a verified sample collection to be tested for DNA specifically. Once a DNA profile is procured, it is added to the secure DNA profile database for future reference.

Step 2: Saliva Collection with Device:

Using the app, or another form of online access or using a paper-based chain of custody form, the collector checks the identification of the donor, records the date and UILN and completes the saliva collection process.

If the device is the Version 1, above, the collector will send all the samples directly to the laboratory for testing.

If the device is Version 2, above, the collector will read the result (take a picture of the result and record the time on the app if preferred by the administrative entity) and per the instructions of the administrative entity, either send all the samples to the laboratory or just specific ones.

Step 3: Laboratory Confirmation:

The laboratory processes the saliva sample for the presence of the drug or substance being tested for.

Depending on the preference of the administrative entity either all processed samples, or only samples with a particular result or a number of random samples are sent for DNA testing either at the same laboratory or a partner laboratory.

Step 4: Test Result Delivery:

Depending on the preference of the administrative entity results will be posted to the secure results database with or without DNA profile matching.

Additional Disclosure

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of." The phrase "one or more of the following: A, B, and C" means "at least one of A and/or at least one of B and/or at least one of C."

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

INDUSTRIAL APPLICABILITY

The invention is applicable to products and methods for saliva-based analyte testing, and more particularly, saliva-based drug testing.

RELATED ART

1. US20030064526A1, Niedbala et al.
2. WO2009073155A2, Wu et al.

| REFERENCE SIGNS LIST |
| --- |
| multi-chamber saliva collection device (10) |
| container (11) |
| well (12) |
| proximal end (13) |
| distal end (14) |
| bifurcating element (15) |
| first chamber (16a) |
| first fluid-aperture (17a) |
| second chamber (16b) |
| second fluid-aperture (17b) |
| fluid communication channel (18) |
| saliva (SA) |
| collection-swab (19) |
| DNA preservation buffer (20) |
| buffer-containing cavity (21) |
| top-plate (22) |
| swab-aperture (23) |
| lateral flow immunochromatographic diagnostic assembly (24) |
| access-port (25) |
| horizontal channel (110) |
| trigger-element (120) |
| protruding end (121) |
| terminal end (122) |
| sleeve-seal (123) |
| protrusion (124) |
| dome having a gradual surface (125) |
| cap-assembly (210) |
| threaded-base (211) |
| cap-element (212) |
| puncture element (213) |
| film-element (214) |
| slot (215) |
| tab (216) |
| first O-ring (217) |
| second O-ring (218) |

-continued

| REFERENCE SIGNS LIST |
| --- |
| third O-ring (219) |
| buffer-ports (220) |
| buffer-channels (221) |
| clips (222) |
| rim (223) |
| chamber-seal (224) |
| receiver (225) |

What is claimed is:

1. A multi-chamber saliva collection device (10), comprising:
a container (11) including:
a well (12) extending within a volume of the container from a proximal end (13) to a distal end (14),
a bifurcating element (15) disposed adjacent to the well at the distal end,
a first chamber (16 a) coupled to the bifurcating element at a first fluid-aperture (17 a), and
a second chamber (16 b) coupled to the bifurcating element at a second fluid-aperture (17 b),
a volume between each of: the well, the first fluid-aperture and the second fluid-aperture collectively defining a fluid communication channel (18);
wherein the container is adapted to receive saliva (SA) upon extraction from a collection-swab (19), and communicate said saliva through the fluid communication channel into each of the first and second chambers;
characterized in that the multi-chamber saliva collection device further comprises:
an amount of DNA preservation buffer (20) contained within a buffer-containing cavity (21);
the buffer-containing cavity being configured to selectively release the DNA preservation buffer for mixing with an aliquot of the saliva in at least one of the first and second chambers;
wherein the multi-chamber saliva collection device is configured to segregate the saliva into at least two aliquots for use in performing an instant analyte test and a subsequent DNA confirmation;
wherein a wall of the first chamber includes a lateral flow immunochromatographic diagnostic assembly (24) that is coupled to the first chamber and is in fluid communication with the first chamber and segregated from the second chamber by a trigger-element, the lateral flow immunochromatographic diagnostic assembly being configured to receive an effective amount of the saliva from the first chamber for completing a lateral flow immunochromatographic diagnostic test and displaying results thereof.

2. The multi-chamber saliva collection device of claim 1, further comprising a top-plate (22), the top-plate embodying a swab-aperture (23), wherein the swab-aperture is configured to pass at least a portion of a collection-swab through a surface of the top-plate.

3. The multi-chamber saliva collection device of claim 2, wherein the proximal end of the well is coupled to the top plate at the swab-aperture.

4. The multi-chamber saliva collection device of claim 3, further comprising an access-port (25) embodied within the container at one of the first and second chambers, wherein the access-port is configured for accessing, from outside the container, the respective aliquot of the saliva contained in the one of the first and second chambers.

5. The multi-chamber saliva collection device of claim 4, further comprising a horizontal channel (110), the horizontal channel coupled to the distal end of the well at a first side of the horizontal channel, and further coupled to the second chamber at a second side of the horizontal channel, wherein the first side of the horizontal channel is opposite the second side; and wherein a volume between each of: the well, the horizontal channel, the first fluid-aperture and the second fluid-aperture collectively defines the fluid communication channel.

6. The multi-chamber saliva collection device of claim 5, wherein the trigger-element (120) includes: a protruding end (121) and a terminal end (122), wherein the protruding end is configured to extend through the container and is configured to be pressed toward the container for translating the trigger-element longitudinally along the horizontal channel, and wherein the terminal end of the trigger-element is configured to be contained within the container and further comprises: the buffer-containing cavity, and the DNA preservation buffer within the buffer-containing cavity.

7. The multi-chamber saliva collection device of claim 6, further comprising a sleeve-seal (123), the sleeve-seal being concentrically nested about the terminal end of the trigger-element and configured to establish a seal for containing the DNA preservation buffer within the buffer-containing cavity.

8. The multi-chamber saliva collection device of claim 7, further comprising a protrusion (124) extending from the container within the fluid communication channel and being disposed adjacent to a terminal end of the horizontal channel, wherein upon translation of the trigger the protrusion is configured to engage the sleeve-seal for releasing the DNA preservation buffer from within the buffer-containing cavity.

9. The multi-chamber saliva collection device of claim 5, wherein the bifurcating element is configured as a dome having a gradual surface (125) for biasing flow of saliva in greater quantity toward the first chamber.

10. The multi-chamber saliva collection device of claim 9, wherein upon releasing the DNA preservation buffer from within the buffer-containing cavity, the container is adapted to communicate the DNA preservation buffer through the fluid communication channel and into the second chamber for mixing with the aliquot of saliva therein.

11. A multi-chamber testing device (10) comprising:
a container (11) including:
a well (12) extending within a volume of the container from a proximal end (13) to a distal end (14),
a first chamber (16 a) in fluid communication with the well via a first fluid-aperture (17 a),
a second chamber (16 b) in fluid communication with the well via a second fluid-aperture (17 b), and
a bifurcating element (15) disposed adjacent to the well at the distal end that directs a first aliquot into the first fluid-aperture and a second aliquot into the second fluid-aperture,
a chamber-seal extending into the container and shiftable from an open position in which the first and second fluid-apertures are in fluid communication with the well and a closed position in which the chamber-seal blocks fluid communication between the first and second chambers and the distal end of the well; and
a cap-assembly (210), the cap-assembly including: a threaded-base (211) and a cap-element (212) coupled thereto; the threaded-base further comprising a puncture element (213); and the cap-element further comprising a film-element (214) sealed along a periphery of the cap-element; wherein a volume between an inside of the cap-element and the film-element defines a buffer-containing cavity (21) containing DNA preservation buffer (20); and wherein upon pressing the cap-element against the threaded-base, the puncture element is adapted to puncture the film-element for releasing the DNA preservation buffer from the buffer-containing cavity into at least one of the first aliquot or the second aliquot.

12. The multi-chamber testing device of claim 11, wherein one of the threaded-base and the cap-element further comprises at least one slot (215), and the other of the threaded-base and cap-element further comprises at least one tab (216), wherein the cap-element is adapted to collapse against the threaded-base only when the at least one tab is rotationally aligned with the at least one slot, and wherein the film-element is adapted to be punctured by the puncture element only when the cap-element is collapsed against the threaded-base.

13. The multi-chamber testing device of claim 12, further comprising:
a top-plate (22) defining a swab-aperture (23) configured to pass at least a portion of a collection-swab (19) through a surface of the top-plate;
a first O-ring (217) configured to be disposed at a distal end of the collection-swab for establishing a first fluid-seal with an inner-surface of the well, a second O-ring (218) configured to be disposed between the threaded-base and the cap-element for establishing a second fluid-seal therebetween, a third O-ring (219) configured to be disposed between the threaded-base and the top-plate for establishing a third fluid-seal therebetween, or a combination thereof.

14. The multi-chamber testing device of claim 13, said threaded-base further comprising one or more buffer-ports (220), and said top-plate further comprising one or more buffer-channels (221) wherein the device is configured to direct a flow of the DNA preservation buffer from the buffer-containing cavity, through the buffer-ports and the buffer-channels, and into at least one of the first and second chambers, wherein the top-plate comprises one or more clips (222) for securing the top-plate to a rim (223) of the container.

15. The multi-chamber testing device of claim 14, wherein the chamber-seal is configured to be pushed into the container from a bottom end thereof, wherein, when pushed into receiver (225) of the container, the chamber-seal is configured to form a seal at each of the first fluid-aperture and the second fluid-aperture.

16. A method for obtaining a result from an analyte test, the method comprising:
providing the multi-chamber saliva collection device of claim 1;
storing an aliquot of a saliva sample and the DNA preservation buffer within at least one of the first and second chambers of the multi-chamber saliva collection device;
providing an instant test result at the lateral flow immunochromatographic diagnostic assembly;
sending the multi-chamber saliva collection device to a laboratory; and
performing a DNA test to confirm a source of the saliva sample.

17. A multi-chamber testing device (10) comprising:
a container (11) including:
a well (12) extending within a volume of the container from a proximal end (13) to a distal end (14),
a first chamber (16 a) in fluid communication with the well via a first fluid-aperture (17 a), a second chamber (16 *b*) in fluid communication with the well via a second fluid-aperture (17 *b*), and a bifurcating element (15) disposed adjacent to the well at the distal end that directs a first aliquot into the first fluid-aperture and a second aliquot into the second fluid-aperture, an amount of DNA preservation buffer (20) contained within a buffer-containing cavity (21), the buffer-containing cavity being configured to selectively release the DNA preservation buffer for mixing with at least one of the first aliquot or the second aliquot; and a chamber-seal extending into the container and shiftable from an open position in which the first and second fluid-apertures are in fluid communication with the well and a closed position in which the chamber-seal blocks fluid communication between the distal end of the well and the first and second fluid-apertures.

18. The multi-chamber testing device of claim 17, further comprising an immunochromatographic diagnostic assembly (24) in fluid communication with the first chamber when the chamber member is in the closed position.

19. The multi-chamber testing device of claim 17, wherein the chamber-seal extends into a bottom of the container toward the distal end of the well and covers the first and second fluid-apertures when the chamber-seal is in the closed position, further comprising:

a threaded-base (211) operable to be seated on the container with a base channel in fluid communication with the well, the threaded-base having a puncture element (213) extending into the base channel; and a cap-element (212) coupled to the threaded-base and comprising a film-element (214) sealed along a periphery of the cap-element, a volume between an inside of the cap-element and the film-element defining the buffer-containing cavity with the DNA preservation buffer being disposed within the buffer-containing cavity, wherein upon pressing the cap-element against the threaded-base, the puncture element is adapted to puncture the film-element for releasing the DNA preservation buffer from the buffer-containing cavity.

\* \* \* \* \*